US009872896B2

(12) United States Patent
Kool et al.

(10) Patent No.: US 9,872,896 B2
(45) Date of Patent: Jan. 23, 2018

(54) IMMORTALIZED PORCINE ALVEOLAR MACROPHAGE (71) Applicant: Intervet Inc., Madison, NJ (US)

(72) Inventors: Jaap Kool, Groesbeek (NL); Carla Christina Schrier, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/102,971

(22) PCT Filed: Dec. 11, 2014

(86) PCT No.: PCT/EP2014/077361
§ 371 (c)(1),
(2) Date: Jun. 9, 2016

(87) PCT Pub. No.: WO2015/086739
PCT Pub. Date: Jun. 18, 2015

(65) Prior Publication Data
US 2016/0303220 A1  Oct. 20, 2016

(30) Foreign Application Priority Data
Dec. 12, 2013 (EP) .................... 13196834

(51) Int. Cl.
| *A61K 39/12* | (2006.01) |
| *C12N 7/00* | (2006.01) |
| *C12N 5/0786* | (2010.01) |
| *C07K 14/005* | (2006.01) |
| *A61K 39/00* | (2006.01) |

(52) U.S. Cl.
CPC ............ *A61K 39/12* (2013.01); *C07K 14/005* (2013.01); *C12N 5/0645* (2013.01); *C12N 7/00* (2013.01); *A61K 2039/5252* (2013.01); *A61K 2039/5254* (2013.01); *C12N 2510/04* (2013.01); *C12N 2770/10034* (2013.01); *C12N 2770/10051* (2013.01); *C12N 2770/10052* (2013.01)

(58) Field of Classification Search
None
See application file for complete search history.

(56) References Cited

U.S. PATENT DOCUMENTS

2010/0083391 A1* 4/2010 Hamilton ........... A01K 67/0271
800/10
2011/0177118 A1* 7/2011 Zuckermann ............ C12N 7/00
424/204.1

FOREIGN PATENT DOCUMENTS

| WO | 2008089094 A2 | 7/2008 |
| WO | 2009024239 A2 | 2/2009 |
| WO | 2012163258 A1 | 12/2012 |

OTHER PUBLICATIONS

Clark et al. (BMC Biotechnology. 2007; 7.1 (42).*
Deepika Ahuja et al, SV40 large T antigen targets multiple cellular pathways to elicit cellular transformation, Oncogene, 2005, pp. 7729-7745, 24.
G. Wensvoort et al, Mystery swine disease in the Netherlands: The isolation of Lelystad virus, Veterinary Quarterly, 1991, pp. 121-130, 13.
Kumar Shanmukhappa et al, Role of CD151, a tetraspanin, in porcine reproductive and respiratory syndrome virus infection, Virology Journal, 2007, p. 62, 4.
Lee, Y.J. et al., Generation of a porcine alveolar macrophage cell line for the growth of porcine reproductive and respiratory syndrome virus, Journal of virological methods, 2010, pp. 410-415, 163.
Mosier DE, et al, Safety Considerations for Retroviral Vectors: A Short Review, Applies Biosafety, 2004, pp. 68-75, 9.
Provost, C. et al., Identification of a new cell line permissive to porcine reproductive and respiratory syndrome virus infection and replication which is phenotypically distinct from MARC-145 cell line, Virology Journal, 2012, pp. 267, 9.
Sagong, M. et al., Human telomerase reverse transcriptase-immortalized porcine monomyeloid cell lines for the production of porcine reproducive and respiratory syndrome virus, Journal of virological methods, 2012, 26-32, 179.
Silversides, DW et al, Investigation of the Species Origin of the St. Jude Porcine Lung Epithelial Cell Line (SJPL) Made Available to Researchers, Journal of virology, 2010, 5454-5455, 84.
Weingartl, H.M. et al., Continuous porcine cell lines developed from alveolar macrophages. Partial characterization and virus susceptibility, Journal of Virological Methods, 2002, pp. 203-216, vol. 104.

* cited by examiner

*Primary Examiner* — Shanon A. Foley (57) ABSTRACT

The present invention relates to immortalized porcine alveolar macrophages (PAMs), to cell cultures comprising such PAMs, to methods for the immortalization of PAMs, to methods of replicating PRRS virus on immortalized PAMs and to methods for the preparation of vaccines comprising PRRSV.

11 Claims, 8 Drawing Sheets

IMMORTALIZED PORCINE ALVEOLAR MACROPHAGE

CROSS-REFERENCE TO RELATED APPLICATIONS

This application is a national stage entry under 35 U.S.C. § 371 of PCT/EP2014/077361 filed on Dec. 11, 2014, which claims priority to EP Application No. EP13196834.9 filed on Dec. 12, 2013. The content of PCT/EP2014/077361 is hereby incorporated by reference in its entirety.

The present invention relates to immortalized porcine alveolar macrophages (PAMs), to cell cultures comprising such PAMs, to methods for the immortalization of PAMs, to methods of replicating PRRS virus on immortalised PAMs and to methods for the preparation of vaccines comprising PRRSV.

Porcine Respiratory and Reproductive Syndrome Virus (PRRSV) is by far the most economically important arterivirus, affecting swine farming industries around the world. Infection with this virus results in slow growth, decreased feed efficiency, anorexia, and fever in weaning to finishing pigs, abortion in pregnant sows and respiratory problems in young pigs. In the US alone, yearly losses associated with PRRSV infection were estimated to lie around $560 million in 2005 and $664 million in 2011. PRRSV infection ranks as the number one health challenge for the pig industry. Considering the emergence of highly virulent strains of PRRSV in South-East Asia in 2006 and the fact that the Asian swine industry is the largest in the world, it can safely be assumed that losses in this part of the world are even considerably higher than those reported for Europe and the US.

PRRSV remains a major threat to the swine industry since the associated disease has proven to be difficult to control, in spite of the availability of both live attenuated and killed vaccines against PRRSV.

For PRRSV vaccine production, live attenuated or inactivated, the virus must be replicated on susceptible cells. One of the problems faced in the propagation of PRRSV is the highly restricted cell tropism of the virus. It mainly infects primary porcine alveolar macrophages (PAMs). Such PAMs are difficult to obtain: they are usually obtained through lung lavage of piglets at usually 6-12 weeks of age (Wensvoort, G. et al., The Veterinary Quarterly 13: 121-130 (1991)). This method is cumbersome, expensive and leads to batches with a high batch-to-batch inconsistency. Moreover, primary PAMs can only be kept in cell culture for a very limited amount of time. Thus, although primary PAMs are very suitable for growing PRRSV, they are only useful in e.g. experimental infection studies and for making experimental vaccines. Production of a commercial vaccine on primary PAMs is economically not feasible.

Due to this problem, scientists have tried to find other cells or better; cell lines, that are susceptible to PRRSV. Only three cell lines have been identified: MA104 monkey kidney cell line and two derivatives of MA104: MARC-145 and CL2621 cells (Kumar Shanmukhappa et al., Virology Journal 2007, 4: 62). These cell lines are currently commercially used for the propagation of PRRSV.

Although it is possible to grow PRRSV to relatively high titers on these cell lines, such non-PAM not even being porcine cell lines have a disadvantage: since they are not the natural host of PRRSV, PRRSV has to be adapted to these cell lines before high titers can be obtained. As a consequence, neither MA104 nor MARC-145 or CL2621 would be the first choice for the propagation of newly discovered field strains. For picking up new PRRSV field isolates the natural host cell, the PAM, would be much more suitable.

It has been contemplated that an immortalized PAM cell line could provide a solution to the problems identified above.

Immortalized PAM cell lines can in principle be grown without limitation to their passage level and they are the most suitable host cells for PRRSV.

Several attempts have been made to develop immortalized PAM cell lines.

PCT Patent Application WO2008/089094 discloses two natural, deliberately non-transformed PAM mutants obtained from porcine fetuses. These cells show immortalized PAM cell line behavior and they are capable of growing PRRSV. The disadvantage of the method described is, that it is a trial-and-error based method of which the outcome is highly uncertain. Specifically it is questionable if any fetal cell line isolated using this method is indeed immortalized in a stable manner or merely has a somewhat extended life span or is capable of dividing just a few more times when compared to a primary PAM. The method is thus unattractive to the skilled person in need of an immortalized PAM cell line.

A Thesis by Jian-Jun Jia (August 2009, Universite de Montreal, Montreal, Canada) describes an allegedly porcine lung cell line susceptible to PRRSV, but this cell line is not an alveolar but an epithelial cell line and furthermore later turned out not to be of porcine origin (D. W. Silversides et al., Journal of virology 84: 5454-5455 (2010)).

A further attempt to make a genuine immortalized PAM cell line is described by H. M. Weingartl et al, in J. Virol. Meth. 104: 203-216 (2002). Weingartl described transfection of primary PAMs with a plasmid pSV3neo, carrying genes for neomycin resistance and SV40 T antigen. This led to the isolation of three myeloid (monocyte/macrophage) immortalized cell lines. The outcome of this experiment however turned out to be enigmatic: no SV40 T Antigen could be detected in any of these cell lines, and moreover, none of the cell lines did support PRRSV replication. Weingartl therefore concludes that an alternative mechanism, not the presence of SV40 T Antigen, may account for the immortalization.

After this failure, the route of using SV40 T antigen was left for alternative approaches. Yoo Jin Lee et al., found that the cell lines developed by Weingartl do not express detectable levels of the 130 kDa cell surface glycoprotein CD163, known to be a cellular receptor for PRRSV (J. Virol. Meth. 163: 410-415 (2010)). Thus, Yoo Jin Lee additionally transfected one of Weingartl's PAM cell lines with the CD163 gene cloned into a retroviral vector under the control of a retroviral LTR promoter. This indeed led to the formation of an immortalized PAM cell line capable of growing PRRSV.

It was concluded in 2012 by Mingeun Sagong of the research group to which Yoo Jin Lee belongs, that the loss of the original properties of primary cells such as PAM-specific markers, e.g. CD163, may be due to transformation with SV40 T antigen (J. of Virological Methods 179: 26-32 (2012)). For that reason an alternative route was followed by Sagong to immortalize PAMs. This route comprises the expression of human telomerase reverse transcriptase (hTERT), using a retroviral vector, in PAMs to restore telomerase activity. The restoration of telomerase activity avoids loss of telomeric DNA and thus avoids replicative senescence of the cells.

Mingeun Sagong concludes that their data revealed that in contrast to SV40 T antigen-transformed PAM cells, hTERT immortalization is capable of rendering the cells reliable representatives of their parental cell's phenotype.

It follows from the above that in order to successfully transform PAMs with the aim of inducing immortalization, regardless the route followed to avoid senescence, the use of SV40 T antigen is to be avoided, and a retrovirus or at least large retroviral sequences must be used to insert the DNA into the genome of the PAMs. A severe disadvantage of the use of retroviruses or at least large retroviral sequences for transforming cells is that in all cases Large terminal Repeat (LTR) sequences are present in the DNA used for the transformation of the cells.

LTRs are retroviral elements that comprise all required signals for retroviral gene expression: enhancer, promoter, transcription initiation, transcription terminator and polyadenylation signal.

These LTRs are suspected of having tumorigenic effects. This is due to the fact that they are known to cis-activate other cellular genes and the fact that they may recombine with other retroviral sequences in the cellular genome (Mosier, D. E., Applied Biosafety 9: 68-75 (2004)).

Nevertheless, transformation of cells with retroviral DNA comprising LTR sequences and avoiding the use of SV40 T antigen seemed to be the only way to obtain immortalized PAMs.

Surprisingly it was found now, that it is possible to successfully obtain PAMs that are immortalized and still susceptible to PRRSV, and nevertheless free of retroviral Long Terminal Repeat DNA.

Such immortalized PAMs according to the invention could unexpectedly be obtained through transfection with DNA comprising SV40 T antigen, now however in combination with the use of a transposon as a means to obtain stable integration in the cellular genome.

Transposons can be viewed as natural DNA transfer vehicles that, similar to integrating viruses, are capable of efficient genomic insertion.

For unknown reasons, the negative effects of SV40 T antigen with or without retroviral DNA as described above can unexpectedly be avoided if cells are transformed using a DNA molecule comprising a gene encoding SV40 T antigen and transposons.

In principle, the transposons remain stably present in the cellular genome after integration in the genome. Therefore, preferably immortalized PAMs according to the invention comprise transposons.

For the purpose of the present invention, an immortalized cell line is a population of cells (in this case PAMs) from a multicellular organism which would normally not proliferate indefinitely but, due to mutation, has evaded normal cellular senescence and instead can keep undergoing division. Such cells have escaped the normal limitation of growth for only a finite number of division cycles.

Methods used for the preparation of an immortalised PAM according to the invention basically comprise the following steps:

a) the step of obtaining a cell-containing bronchoalveolar lavage sample from a porcine subject. Such steps have been described already by i.a. Wensvoort, G. et al., in 1991 (vide supra), by Weingartl, H. M. et al. (vide supra), and by others and they are still the preferred way of obtaining PAMs.

b) the step of separating a cellular component from said sample. This step is also well-known in the art, and is also described i.a. by Wensvoort and by Weingartl, and it is usually done through centrifugation of the lung lavage material at low speed, c) the step of transfecting said cellular component with a DNA molecule comprising transposons and comprising a gene encoding the SV40 T antigen under the control of a suitable promoter.

Transfection can be done in many ways known in the art. Commercial kits for transfection are currently available through i.a. Bio-Rad (Life Science (Research, Education, Process Separations, Food Science), Life Science Research, 2000 Alfred Nobel Drive, Hercules, Calif. 94547, USA) and Invitrogen (Life Technology, 3175 Staley Road, Grand Island, N.Y. 14072, USA). Commonly used reagent-based transfection methods comprise the use of lipids, calcium phosphate, cationic polymers, DEAE-dextran, activated dendrimers and magnetic beads. Instrument-based methods comprise electroporation and micro-injection.

A DNA molecule comprising transposons and comprising a gene encoding the SV40 T antigen under the control of a suitable promoter could e.g. be a plasmid comprising a gene encoding the SV40 T antigen under the control of a suitable promoter. This plasmid may be in a circular or linear form when it is used for the transfection step.

The use of transposons as such is well-known in the art. A paper by Ivics, Z. and Izsvak Z. extensively reviews transposons and their use, and provides insight in the mechanisms of action of transposons (Mobile DNA 1: 25-39 (2010)).

A review paper by Deepika Ahuja et al., about SV40 T antigen provides insight in the mechanisms of action of this protein (Oncogene 24: 7729-7745 (2005)). Basically, SV40 T antigen inhibits the p53 and Rb-family of tumor suppressors. It is this activity of the T antigen that is thought to cause transformation of the cells towards their immortalized character.

A large number of suitable promoters for the expression of the SV40 T antigen are known in the art, which are recognized for their efficient level of expression. They include classic promoters such as the (human) cytomegalovirus immediate early promoter (Seed, B. et al., Nature 329, 840-842, 1987; Fynan, E. F. et al., PNAS 90, 11478-11482, 1993; Ulmer, J. B. et al., Science 259, 1745-1748, 1993), the Human Cytomegalovirus enhancer-promoter for the expression of gD of BoHV-1. (Donofrio G., et al., Clinical and Vaccine Immunology 13: 1246-1254, (2006)), the Mouse Cytomegalovirus immediate early (MCMViel) promoter, the Mouse Cytomegalovirus early (MCMVel) promoter, SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992).

A preferred promoter is the CAG promoter. (Miyazaki, J; Takaki, S; Araki, K; Tashiro, F; Tominaga, A; Takatsu, K; Yamamura, K., Gene 79 (2): 269-77 (1989), and Niwa, H; Yamamura, K; Miyazaki, J. Gene 108 (2): 193-9 (1991).)

d) the step of selecting cells that are capable of sustained proliferation.

PAM cells that are capable of sustained proliferation are cells that have been cultured for at least 5 cell cycles. The cell cycle, or cell-division cycle, is the series of events that take place in a cell leading to its division and duplication (the cell replication). The selection of cells that are capable of sustained proliferation is a very simple process for the following reason: primary PAMs are hardly or not capable of dividing outside their natural environment; the porcine lung. As can be seen from FIG. 2, first 2 bars (no M-CSF added) the number of live primary PAM cells after lung lavage and isolation decreases over time. In a culture starting with 200000 PAM cells, only about half of the cells are still viable after 3 days. This amount further decreases steadily over time.

This means that if there is an increase in the number of cells, this must be due to the fact that one or more cells have successfully been transfected with the DNA molecule comprising the transposon and the gene encoding the SV40 T antigen is inserted in the cellular genome. So basically the process is self-selecting: maintenance of PAMs that were successfully transformed in a suitable cell growth medium will automatically lead to replication of successfully transformed cells, whereas non-immortalised cells will stop dividing and die off. Suitable cell growth media are known in the art and are described i.a. in the Examples section. They are also described i.a. by Wensvoort, G. et al., in 1991 (vide supra), by Weingartl, H. M. et al. (vide supra). Further guidance about cell culture conditions can be found in the Examples.

Thus, one embodiment of the present invention relates to a method for the preparation of an immortalised PAM, wherein said method comprises the steps of
  a) obtaining a cell-containing bronchoalveolar lavage sample from a porcine subject,
  b) separating a cellular component from said sample,
  c) transfecting said cellular component with a DNA molecule comprising transposons and comprising a gene encoding the SV40 T antigen under the control of a promoter, and
  d) selecting cells that can be cultured for at least 5 cell cycles Usually, cells are selected that have been cultured for at least 5 cell cycles. For such cells it can reasonably be assumed that they are successfully immortalized PAMs, since primary PAMs will usually not replicate more than one or two times, exceptionally up to 5 times, in vitro after isolation from the lungs.

In exceptional cases, early cell cycles may show instable behavior, e.g. due to the fact that the transposon has integrated in the cellular genome at a very critical site, or due to instable integration of the gene encoding the SV40 T antigen. Therefore, in practice cells are selected that have been cultured for at least 10, 15, 20, 25, 30, 40, 50 or even 60 cell cycles in that order of preference.

The chances of any instability becoming manifest do decrease with the amount of cell cycles of the selected immortalised PAM.

Thus, preferably, cells are selected that have been cultured for at least 10, 15, 20, 25, 30, 40, 50 or even 60 cell cycles in that order of preference.

The presence of Macrophage Colony Stimulating Factor (M-CSF) does not significantly stimulate replication of primary PAMs for more than a few cell divisions.

The presence of granulocyte-M-CSF (gM-CSF) may improve the condition of the primary PAMs, even to the extent that there is some replication for a very short period of time. It was however shown by the inventors that the use of gM-CSF leads to a decrease in CD163-expression. And since CD163 is involved in the replication of PRRSV to PAMs, the use of gM-CSF may in this respect not have a nett beneficial effect.

M-CSF appears to improve the condition of the primary PAMs to a lesser extent than gM-SCF, but it does not interfere with CD163-production.

It was however surprisingly found that the presence of M-CSF in the growth medium of PAMs obtained through lung lavage, before they are subjected to transfection, makes the cells somewhat better resistant to the stressful process of transfection. Thus, the efficiency of transfection is significantly increased in the presence of M-CSF.

Suitable amounts of M-CSF are e.g. 5, 10, 25, 50, 100 or 200 ng/ml in that order of increasing order of preference.

Figure 2:
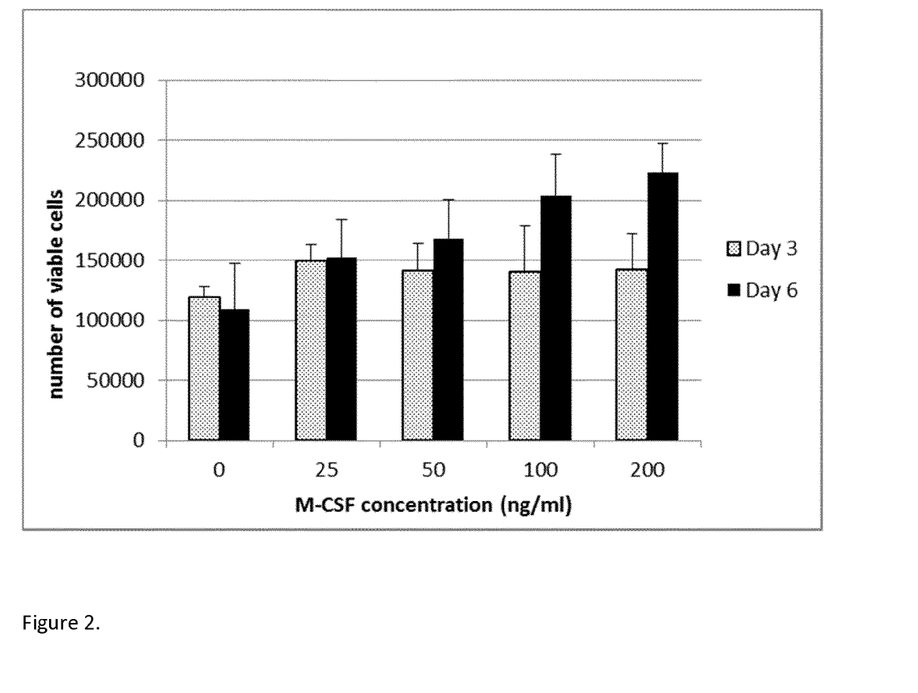
FIG. 2: M-CSF increases in vitro survival of primary PAMs. 200000 cells primary PAM cells were seeded in duplo at t=0 (day 0) in medium containing no or different concentrations of M-CSF. The number of viable cells was determined at 3 and 6 days after seeding. Cell numbers were determined in duplo per well. Data depicted are mean+SEM of four independent measurements.

(In FIG. 2 it can be seen that indeed in the presence of M-CSF, the number of live primary PAMs cells after lung lavage and isolation decreases (or at best stays stable for 6 days). The decrease is less dramatic over time when compared to the decrease in the absence of M-CSF, but in any case there is within the statistical probability no increase in the number of cells).

Therefore, another preferred form of this embodiment relates to methods according to the invention, wherein the method comprises the step of adding an amount of at least 5 ng/ml of M-CSF to the cell-containing bronchoalveolar lavage sample and/or the cellular component before the transfection step. PCT Patent Application WO2008/089094 discloses the use of M-CSF as a mandatory growth medium component in order to keep immortalized but non-transformed fetal PAMs alive. Contrary to this, in the present invention M-CSF or gM-CSF is used before the PAMs are immortalized.

It was shown by the inventors that unexpectedly the presence of M-CSF during step d) and/or while culturing immortalised PAMs according to the invention, i.e. transformed and non-fetal PAMs, also improves the viability of these transformed and non-fetal cells according to the invention. It can be seen in FIG. 4, that both the viability and replication rate of immortalized PAMs according to the invention improves significantly in the presence of M-CSF. Small amounts of M-CSF of a magnitude of 1, 2, 3, 4 or 5 ng/ml already suffice to improve both viability and replication rate. Preferred concentrations of M-CSF are 6, 12, 25, 50, 100, 200 or even 400 ng/ml, in increasing order of preference.

Thus, again another preferred form of this embodiment relates to a method according to the invention wherein the method additionally comprises the step of adding an amount of at least 1 ng/ml of M-CSF during step d) and/or while culturing the immortalised PAM according to the invention.

Figure 5:
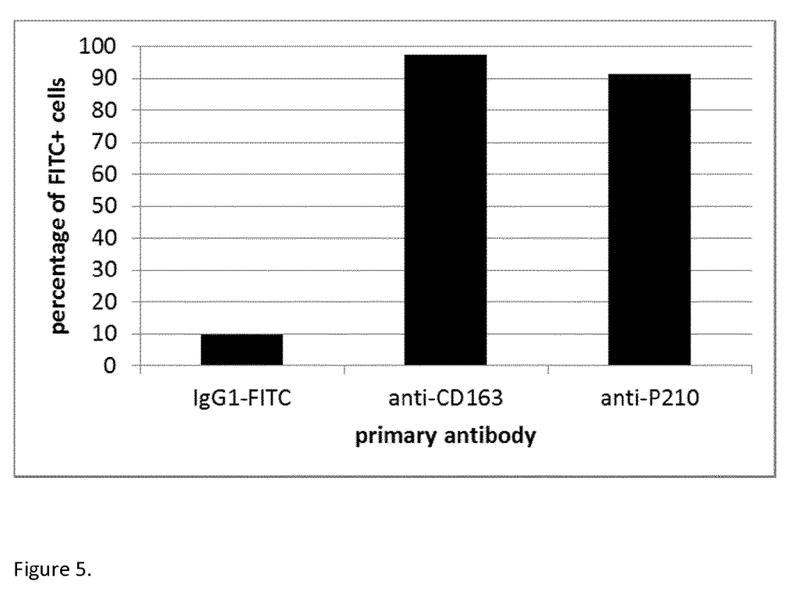
FIG. 5: PAM SVh cells express CD163 and sialoadhesin. PAMSVh cells were labeled with antibodies raised against CD163 or p210 or isotype control antibodies. Cells were labeled with FITC-labeled secondary antibodies and analyzed by flow cytometry. The percentage of FITC-positive cells per antibody is depicted.

FIG. 5 shows that antibodies against CD163 and P210, two receptors that were demonstrated to be essential for entry and replication of PRRS virus in PAM cells, are indeed reactive with immortalized PAMs according to the invention. This means that CD163 and P210 are indeed present on immortalized PAMs according to the invention.

Figure 6:
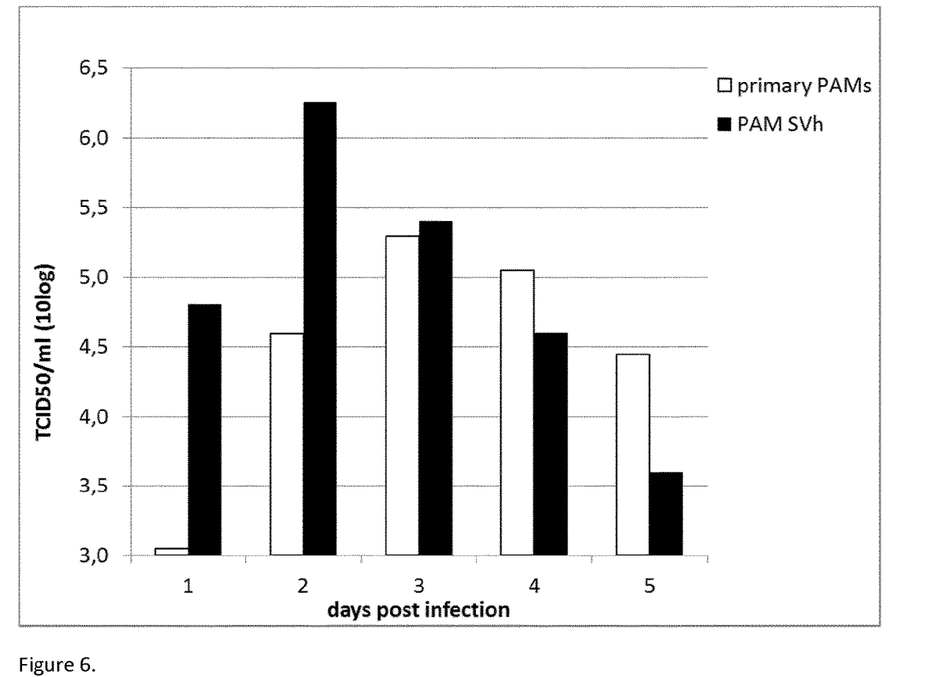
FIG. 6: PRRSV replication on PAM SVh cells. Cells were infected at t=0 with a pathogenic PRRSV field isolate (MOI 0,001). Supernatants were harvested at different days after infection and titrated to determine virus titers. The 10 log values of the TCID50/ml are depicted for primary PAMs (open bars) and PAM SVh (solid bars). Data are mean of two independent titrations.

FIG. 6 shows that immortalized PAMs according to the invention indeed support PRRSV replication. It can be seen, that a PRRSV field isolate replicates even faster and to a higher titer in the first 2-3 days after infection, when compared with primary PAMs.

FIG. 7 shows, that indeed a PRRSV field isolate replicates faster and to a higher titer on immortalized PAMs according to the invention, when compared to replication on MARC-145 cells. It can also be seen that a field isolate indeed replicates better on PAMs in general, regardless if they are immortalized or not, when compared to replication on MARC-145 cells.

FIG. 7 also shows that vice versa PRRSV Type I and Type II strains that are adapted to replication on MARC-145 cells replicate to a higher titer on MARC-145 cells when compared to replication on PAMs.

This shows that indeed immortalized PAMs according to the invention are as suitable as primary PAMs to replicate PRRSV field isolates, and are thus more suitable to this end than non-PAM cells such as MA104, MARC-145 or CL2621 cells.

A second embodiment of the present invention relates to an immortalised porcine alveolar macrophage (PAM), characterized in that the PAM is susceptible to Porcine Respiratory and Reproductive Virus (PRRSV), the PAM expresses an SV40 T antigen and the PAM does not comprise retroviral Long Terminal Repeat DNA.

Immortalised PAMs according to the invention can in principle further be provided with a functional gene encoding human telomerase reverse transcriptase (hTERT). This is however by no means necessary, since the SV40 T antigen is capable of maintaining the immortalized status of the PAMs according to the invention. In fact, if only for technical simplicity of producing immortalised PAMs, it is preferred that only SV40 T antigen is used for the immortalization of the cells.

Thus, a preferred form of this embodiment relates to immortalised PAMs according to the invention that are characterized in that the PAMs do not comprise hTERT.

A third embodiment of the present invention relates to methods of replicating PRRS virus, characterized in that such methods comprise the steps of
a) culturing an immortalised PAM according to the invention,
b) contacting the immortalised PAM with the PRRS
c) allowing the PRRSV to replicate and
d) isolating the progeny virus.

A fourth embodiment of the present invention relates to a cell culture comprising an immortalised PAM according to the invention.

In a preferred form of this embodiment, the cell culture comprising the immortalised PAM is infected with PRRSV.

In another preferred form of this embodiment, the cell culture comprising the immortalised PAM comprises M-CSF.

A fifth embodiment of the present invention relates to methods for the preparation of a vaccine comprising PRRSV, characterized in that the methods comprise the method of replicating PRRSV according to the invention followed by the step of mixing the virus with a pharmaceutically acceptable carrier.

In a preferred form of this embodiment, the PRRSV is in a live attenuated or an inactivated form.

EXAMPLES

Example 1

Materials and Methods

Plasmids.

Figure 1:
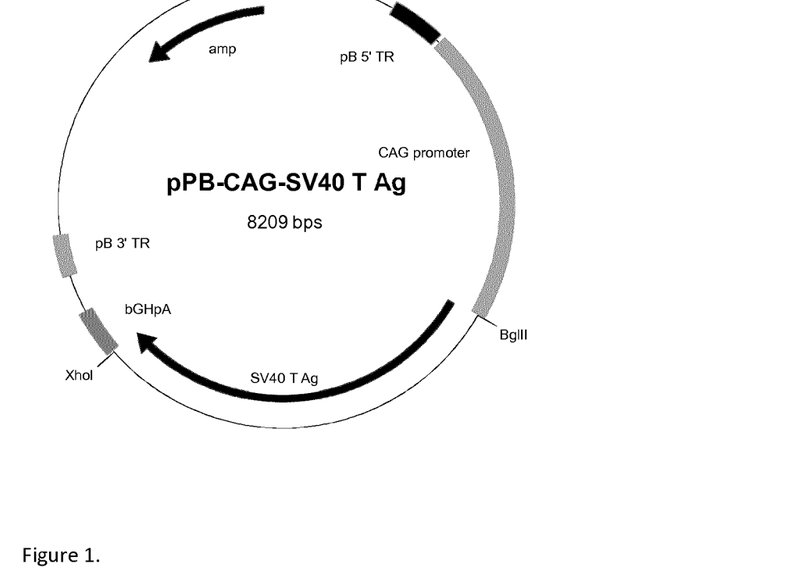
FIG. 1: Vector map pPB-CAG-SV40 T Ag

To construct pPB-CAG-SV40 T Ag, XhoI and BIII sites were added to SV40 T Ag by PCR using primers SV40 Tag 5'-BII (5'-GGCGAGATCTACCATGGATAAAGTTT-TAAACAG-3') and SV40 Tag 3'-XI (5'-GGCGCTCGAGT-TATGTTTCAGGTTCAGGGG-3'). Phusion DNA polymerase was used for PCR according to the manufacturer's protocol (New England Biolabs). The fragment was cloned into pCR-Blunt (Life Technologies) and verified by sequencing. Next, SV40 T Ag was excised from pCR-Blunt and cloned into pPB-CAG-EBNXN (Yusa et al., 2009) using the BIII-XhoI sites to create pPB-CAG-SV40 T Ag (FIG. 1). The final construct was verified by sequencing. Plasmid DNA for transfection into primary PAM cells was isolated with the Qiagen EndoFree plasmid maxi kit (Qiagen).

Isolation and Growth of Primary Cells and PAM SVh Cells.

Porcine alveolar macrophages were harvested from the lungs of 1-2 week old PRRSV-negative, SPF piglets. The lungs were washed three to five times with sterile phosphate-buffered saline (PBS) solution. The washing fluid was centrifuged 10' at 1000×g at 4° C. to pellet cells. Cells were resuspended and stored in liquid nitrogen in RPMI 1640+ HEPES+GlutaMax (Life Technologies) containing 50% FCS (Hyclone, Thermo Scientific), 1x non-essential amino acids (Life Technologies), 2 mM glutamine, antibiotics and 10% DMSO. Upon thawing, PAM cells were taken into culture and grown in RPMI 1640+HEPES+GlutaMax (Life Technologies) containing 20% FCS (Hyclone, Thermo Scientific), 1× non-essential amino acids (Life Technologies), 2 mM glutamine, antibiotics at 37° C. and 5% $CO_2$. Recombinant human M-CSF (M-CSF) was purchased from R&D Systems. PAM SVh cells were grown in medium+100 ng/ml M-CSF (R&D Systems).

Viability Assays.

The effect of M-CSF on in vitro survival of primary PAM cells was examined by seeding 200.000 cells per 24-well in medium containing different concentrations of M-CSF. Each condition was tested in duplo. Cell samples were taken from the wells 3 and 6 days after seeding and the number of viable cells was determined with the GUAVA Easycyte plus (Guava Millipore) using Viacount dye (Guava Millipore) according to the manufacturer's protocol. Each sample was counted twice.

The effect of M-CSF concentration on PAM SVh proliferation was examined in similar fashion with minor adjustments. Here, 25000 cells were seeded in ultra-low attachment 96-well plates and cells were harvested for counting 3, 4, 5 and 6 days after seeding. Each sample was counted twice.

Transfection.

After 6 days in culture, primary PAM cells were harvested and viable cells were counted. In this experiment M-CSF (100 ng/ml) was added to the medium to promote in vitro survival of primary PAMs. Per transfection, 1.10E6 viable cells were transfected in 100 µl Primary cell buffer P3+ supplement (Lonza Cologne AG) using program DN-100 of the Nucleofector 4D (Lonza Cologne AG). Cells were either transfected with 1.6 µg pPB-CAG-SV40 T Ag and 0.4 µg pPB-CMV-hyPBase (Yusa et al., 2011) or, as a control, with 1.6 µg pPB-CAG-EBNXN and 0.4 µg pPB-CMV-hyPBase. After administration of the Nucleofection pulse, cells were left at RT for 10 min. Next, 400 µl RPMI 1640 (37° C.) was slowly added to the cells and cells were incubated at 37° C. for 5 minutes. Then, cells were carefully resuspended, seeded in RPMI 1640+HEPES+GlutaMax (Life Technologies) containing 20% FCS (Hyclone, Thermo Scientific), 1× non-essential amino acids (Life Technologies), 2 mM glutamine, antibiotics and 100 ng/ml M-CSF (R&D Systems) and incubated at 37° C. and 5% CO2.

Antibodies and Flow Cytometry.

Cells were labeled with mouse monoclonal antibodies raised against porcine CD163 (clone 2A10/11, AbD Serotec), mouse monoclonal antibodies raised against porcine sialoadhesin/p210 (Duan et al., 1998) or FITC-labeled mouse IgG1 isotype control antibodies (AbD Serotec). After washing, cells labeled with anti-CD163 or anti-sialoadhesin/p210 antibodies were labeled with FITC-labeled goat-anti-mouse antibodies (Lifespan Biosciences). Cells were analyzed using a Becton Dickinson FACS Calibur cytometer and CellQuest Pro software.

PRRSV Replication and Titration.

To compare primary PAMs, PAM SVh or MARC-145 cells as substrates for PRRSV replication, equal amounts of cells were seeded in 12-wells. Cells were infected at t=0 with either a pathogenic field isolate, a Type I vaccine strain or a Type II vaccine strain with MOI 0,001 or MOI 0,0001. Supernatants were harvested several days after infection and stored at −20° C. Virus titers were determined by titrating primary PAM and PAM SVh supernatants on primary PAMs and MARC-145 supernatants on MARC-145 cells. All titrations were performed in duplo. Titers were calculated using the method of Spearman-Kärber and expressed as $\log_{10}TCID_{50}/ml$.

Results:

M-CSF Promotes In Vitro Viability of Primary PAMs.

Primary PAMs have a low in vitro survival rate in standard RPMI 1640 medium containing 20% FCS (FIG. 2). The number of viable cells declines in time and only about 50% of cells is still viable after three days. Addition of macrophage-colony stimulating factor (M-CSF) to the culture medium has a positive effect on survival and clearly increases the number of viable cells after three or six days compared to cells grown in absence of M-CSF.

Establishment of an SV40-Immortalized PAM Cell Line.

Figure 3:
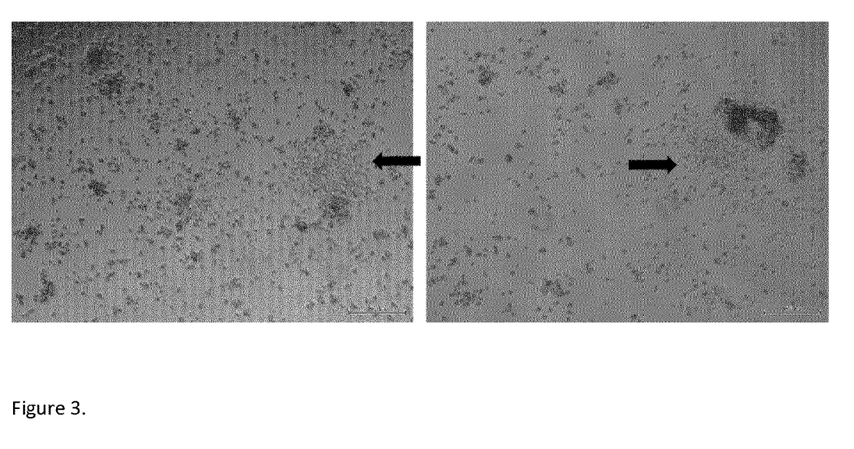
FIG. 3: Colony formation in pPB-CAG-SV40 T Ag transfected cells Colonies are indicated by black arrows.

Primary cells were grown for 6 days in medium with M-CSF and subsequently transfected with pPB-CAG-SV40 T Ag or pPB-CAG-EBNXN in combination with the pPB-CMV-hyPBase vector encoding the piggyBac transposase. After transfection, cells were carefully monitored each day for proliferation and the medium was replenished regularly with fresh medium+100 ng/ml M-CSF. No cell proliferation was visible in the pPB-CAG-EBNXN transfected control cells and 4-5 weeks after transfection all cells were dead. In contrast, small colonies grew out in the cultures of pPB-CAG-SV40 T Ag transfected cells 3-4 weeks after transfection (FIG. 3). These colonies continued to proliferate and were passaged to increase cell number. All cells were SV40 T Ag positive as demonstrated by immunofluorescence (data not shown).

These cells continue to proliferate, can be passaged twice a week and have currently been kept in culture for more than 8 months (50-60 passages). This cell line can easily be regrown in culture after liquid nitrogen storage. The thus established cell line was named PAM SVh.

Proliferation of PAM SVh Cell Line Depends on M-CSF-Concentration.

Figure 4:
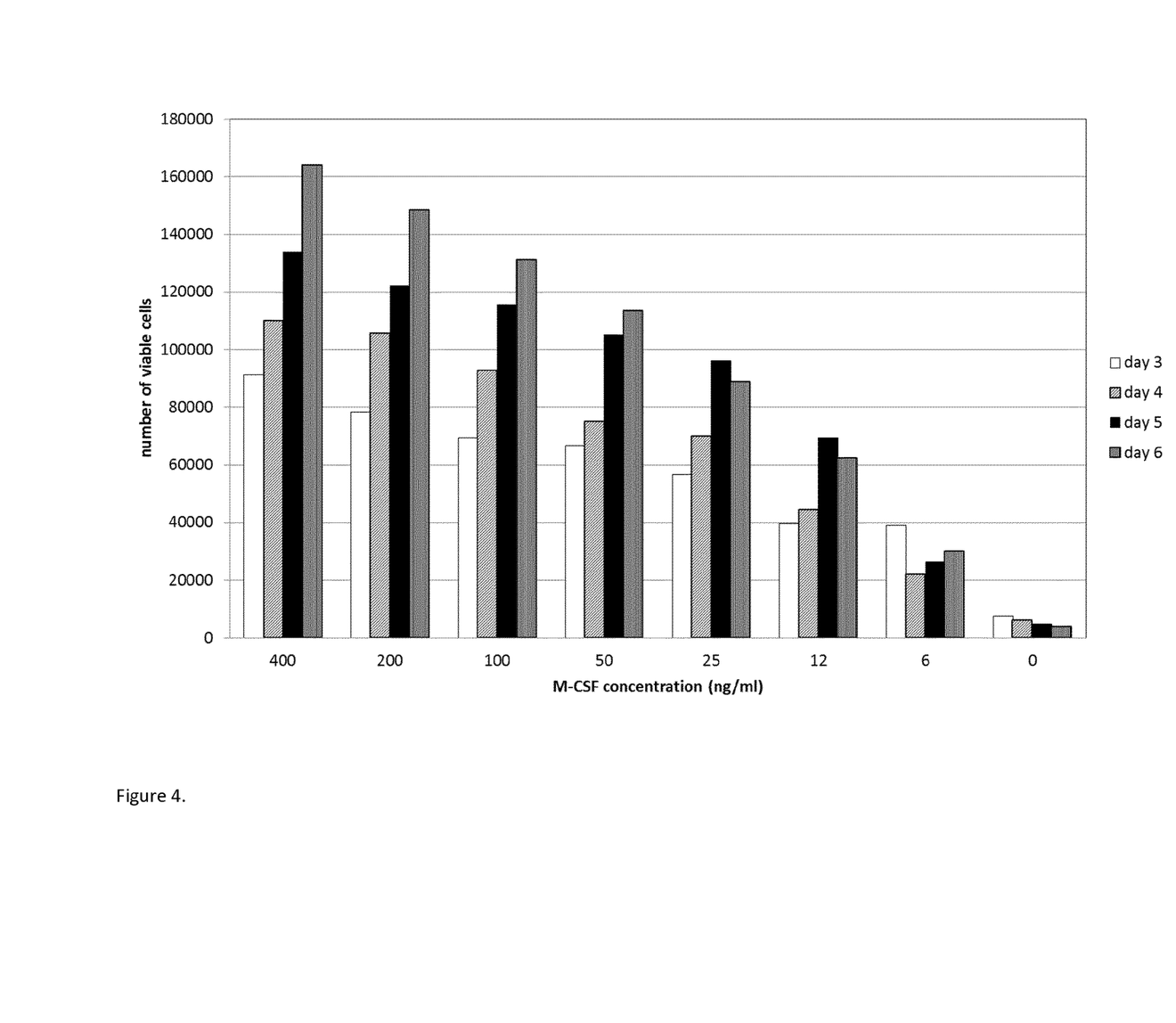
FIG. 4: M-CSF stimulates proliferation of PAM SVh cells. 25000 cells PAM SVh cells were seeded at t=0 (day 0) in medium containing no or different concentrations of M-CSF. The number of viable cells was determined 3, 4, 5 and 6 days after seeding. Data depicted are mean of two cell counts per well.

To determine whether the PAM SVh cell line requires M-CSF for proliferation, PAM SVh cells were grown without or in the presence of different concentrations of M-CSF. The number of viable cells was determined 3 and 6 days after seeding. Proliferation of PAM SVh is M-CSF-dependent in a concentration-dependent manner (FIG. 4). The largest increase in cell number is seen in the presence of high concentrations (400-100 ng/ml) of M-CSF. Lower concentrations of M-CSF result in reduced proliferation of cells and little or no increase in cell number was detected in the absence of M-CSF, indicating that proliferation of PAM SVh cells depends on M-CSF concentration in the medium.

PAM SVh Cells Express Sialoadhesin/p210 and CD163 Markers.

Two receptors have been demonstrated to be essential for entry and replication of PRRS virus in PAM cells, sialoadhesin/P210 and CD163. Whereas expression of sialoadhesin/p210 was found to be essential for binding and entry of PRRSV (in)to PAM cells, CD163 was shown to be required for PRRSV replication in cells (Delputte et al., 2005; Van Gorp et al., 2008; Calvert et al., 2007). We examined whether PAM SVh cells expressed sialoadhesin/P210 and CD163 by labeling cells with specific antibodies raised against these receptors and analyzing them by flow cytometry. More than 80% of PAM SVh cells were found to be CD163+ and more than 70% sialoadhesin/P210+(FIG. 5), suggesting that these cells might be suitable for infection with and replication of PRRSV.

PAM SVh Cells are Suitable Substrates for PRRSV Replication.

We tested whether PAM SVh cells are a substrate for PRRSV replication by infecting them with a pathogenic field isolate. Supernatants were harvested at different days after infection and titrated to determine virus titers. For comparison, we also infected primary PAM cells in the same experiment. PAM SVh cells were infected by the PRRSV field isolate and clearly produce PRRSV virus (FIG. 6). Compared to primary PAMs, virus titers produced by PAM SVh cells were higher at day 1 and day 2 after infection, comparable at day 3 and day 4 and lower at day 5.

Figure 7A:
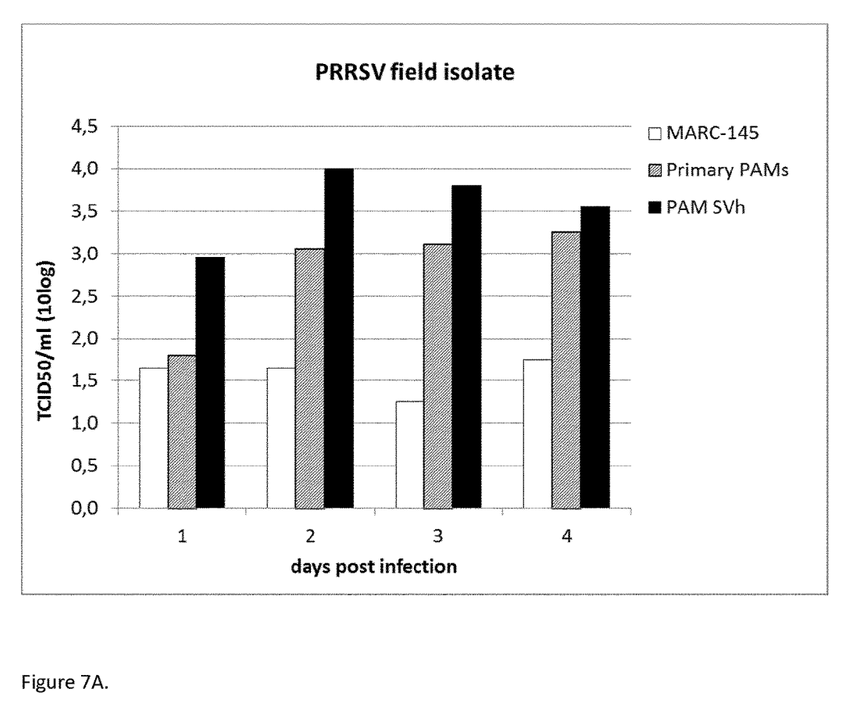
FIG. 7: Replication of different PRRSV strains on PAM SVh cell line. Cells were infected at t=0 with either (A) a pathogenic PRRSV field isolate (MOI 0,0001), (B) PRRSV Type I vaccine strain (MOI 0,001) or (C) PRRSV Type II vaccine strain (MOI 0,001). Supernatants were harvested at different days after infection and titrated to determine virus titers. The 10 log values of the TCID50/ml are depicted for MARC-145 (open bars), primary PAMs (shaded bars) and PAM SVh (solid bars). Data are mean of two independent titrations
Figure 7B:
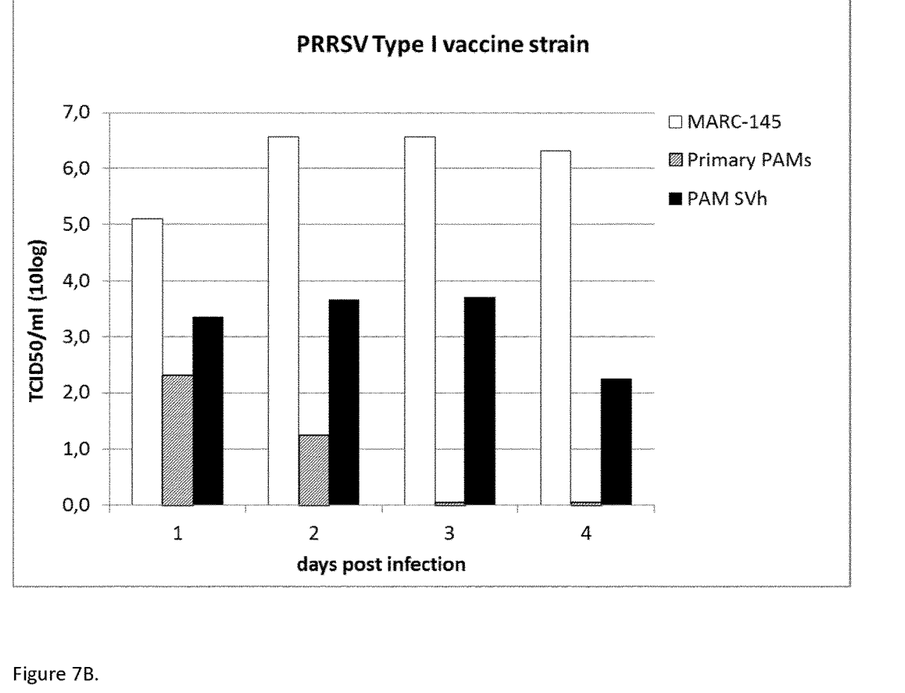
Figure 7C:
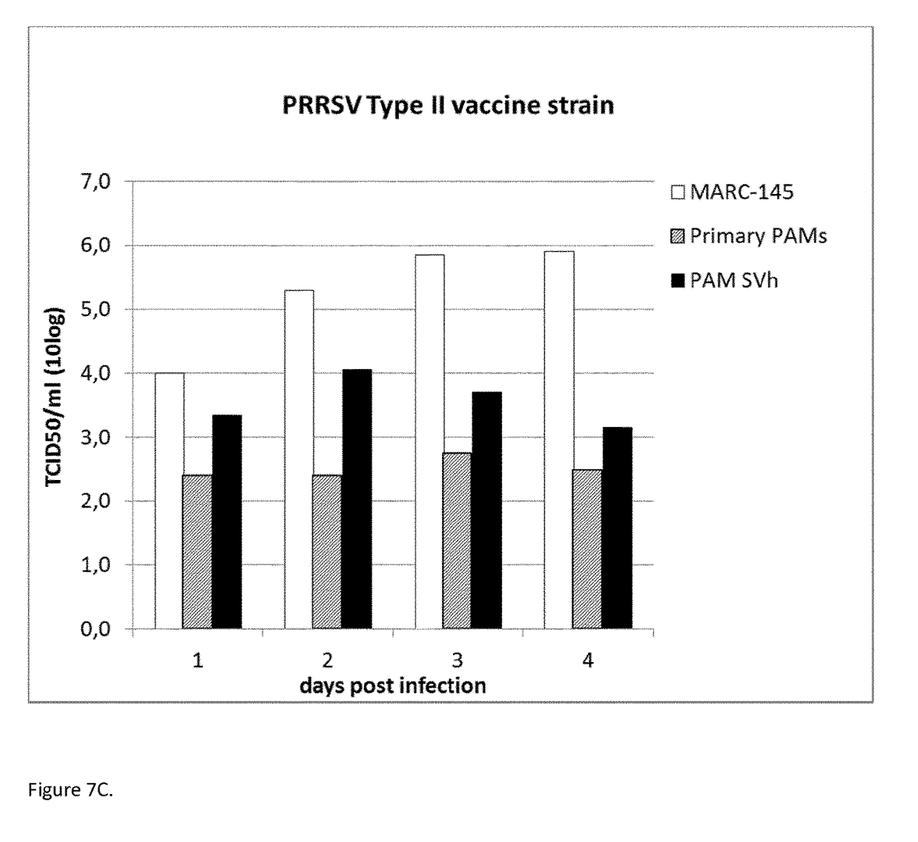

MARC-145 cells are commonly used as substrate for production of PRRSV vaccine strain viruses. We compared primary PAMs, PAM SVh cells and MARC-145 cells as substrates for replication of different PRRSV strains. We infected equal numbers of primary PAMs, PAM SVh and MARC-145 cells with either a pathogenic field isolate, a PRRSV Type I vaccine strain or a PRRSV Type II vaccine strain. Supernatants were harvested at different days after infection and supernatants were titrated to determine virus titers. Again, PAM SVh cells produce comparable or higher titers of the PRRSV field isolate than primary PAMs (FIG. 7A). PAM SVh also produce higher titers of the PRRSV field isolate than MARC-145 cells. When we compared virus titers of the PRRSV Type I and II strains produced on the different substrates, we found that both strains replicated best on MARC-145 cells, the substrate which is normally used for production of these attenuated viruses (FIGS. 7B and C). PAM SVh cells, however, produced higher titers than primary PAMs for both vaccine strains at all timepoints, again demonstrating that PAM SVh cells are a better substrate for PRRSV replication than primary PAMs.

REFERENCE LIST

Calvert, J. G., Slade, D. E., Shields, S. L., Jolie, R., Mannan, R. M., Ankenbauer, R. G., and Welch, S. K. (2007). CD163 expression confers susceptibility to porcine reproductive and respiratory syndrome viruses. J. Virol. 81, 7371-7379.

Delputte, P. L., Costers, S., and Nauwynck, H. J. (2005). Analysis of porcine reproductive and respiratory syndrome virus attachment and internalization: distinctive roles for heparan sulphate and sialoadhesin. J. Gen. Virol. 86, 1441-1445.

Duan, X., Nauwynck, H. J., Favoreel, H. W., and Pensaert, M. B. (1998). Identification of a putative receptor for porcine reproductive and respiratory syndrome virus on porcine alveolar macrophages. J. Virol. 72, 4520-4523.

Van Gorp, H., Van Breedam, W., Delputte, P. L., and Nauwynck, H. J. (2008). Sialoadhesin and CD163 join forces during entry of the porcine reproductive and respiratory syndrome virus. J. Gen. Virol. 89, 2943-2953.

Yusa, K., Rad, R., Takeda, J., and Bradley, A. (2009). Generation of transgene-free induced pluripotent mouse stem cells by the piggyBac transposon. Nat. Methods 6, 363-369.

Yusa, K., Zhou, L., Li, M. A., Bradley, A., and Craig, N. L. (2011). A hyperactive piggyBac transposase for mammalian applications. Proc. Natl. Acad. Sci. U.S.A 108, 1531-1536.

Okabe M, Ikawa M, Kominami K, Nakanishi T, Nishimune Y. 'Green mice' as a source of ubiquitous green cells. FEBS Left. 1997 May 5; 407(3):313-9.

Alexopoulou A N, Couchman J R, and Whiteford J R. The CMV early enhancer/chicken beta actin (CAG) promoter can be used to drive transgene expression during the differentiation of murine embryonic stem cells into vascular progenitors. BMC Cell Biology 9: 2, 2008.

The invention claimed is:

1. A method of isolating progeny PRRSV from an immortalized porcine alveolar macrophage (PAM), wherein said PAM is susceptible to Porcine Respiratory and Reproductive Virus (PRRSV), expresses an SV40 T antigen, and does not comprise retroviral Long Terminal Repeat DNA capable of retroviral gene expression; wherein said method comprises the steps of:
   a) obtaining a cell-containing bronchoalveolar lavage sample from a porcine subject,
   b) separating a cellular component from said sample,
   c) transfecting said cellular component with a DNA molecule comprising transposons and comprising a gene encoding the SV40 T antigen under the control of a suitable promoter,
   d) selecting immortalized PAM cells that have been cultured for at least 5 cell cycles,
   e) further culturing the selected immortalized PAM cells,
   f) contacting the immortalized PAM cells with the PRRSV,
   g) allowing the PRRSV to replicate and form progeny PRRSV, and
   h) isolating the progeny PRRSV.

2. The method of claim 1, wherein PAM cells are selected that have been cultured for at least 10 cell cycles.

3. The method of claim 2, wherein said method additionally comprises the step of adding an amount of at least 1 ng/ml of macrophage colony stimulating factor (M-CSF) during step d) and while culturing the immortalized PAM.

4. The method of claim 1, further comprising mixing the isolated progeny PRRSV of step h) with a pharmaceutically acceptable carrier; wherein the PRRSV and the progeny PRRSV are in a live attenuated form.

5. The method of claim 1, further comprising the step of inactivating the progeny PRRSV after step g) and mixing the inactivated progeny PRRSV with a pharmaceutically acceptable carrier.

6. The method of claim 1, further comprising the step of inactivating the progeny PRRSV after step h) and mixing the inactivated progeny PRRSV with a pharmaceutically acceptable carrier.

7. The method of claim 1, wherein said method further comprises the step of adding an amount of at least 5 ng/ml of macrophage colony stimulating factor (M-CSF) to the cell-containing bronchoalveolar lavage sample, the cellular component, or both the cell-containing bronchoalveolar lavage sample and the cellular component before the transfection step.

8. The method of claim 1, wherein said method additionally comprises the step of adding an amount of at least 1 ng/ml of macrophage colony stimulating factor (M-CSF) during step d) or while culturing the PAM.

9. The method of claim 8 further comprising mixing the isolated progeny PRRSV of step h) with a pharmaceutically acceptable carrier; wherein the PRRSV and the progeny PRRSV are in a live attenuated form.

10. The method of claim 8, further comprising the step of inactivating the progeny PRRSV after step a) and mixing the inactivated progeny PRRSV with a pharmaceutically acceptable carrier.

11. The method of claim 8, further comprising the step of inactivating the progeny PRRSV after step h).

\* \* \* \* \*

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
ggcgagatct accatggata aagttttaaa cag                              33

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ggcgctcgag ttatgtttca ggttcagggg                                  30
```